(12) United States Patent
Baxter et al.

(10) Patent No.: US 11,878,105 B2
(45) Date of Patent: Jan. 23, 2024

(54) SYSTEM AND METHOD FOR POST-OCCLUSION SURGE MITIGATION

(71) Applicant: Alcon Inc., Fribourg (CH)

(72) Inventors: Vincent A Baxter, Temecula, CA (US); David Dyk, Foothill Ranch, CA (US); Satish Yalamanchili, Irvine, CA (US); Raphael Gordon, Ladera Ranch, CA (US)

(73) Assignee: Alcon Inc., Fribourg (CH)

( * ) Notice: Subject to any disclaimer, the term of this patent is extended or adjusted under 35 U.S.C. 154(b) by 78 days.

(21) Appl. No.: 17/393,437

(22) Filed: Aug. 4, 2021

(65) Prior Publication Data

US 2022/0047796 A1 Feb. 17, 2022

Related U.S. Application Data

(60) Provisional application No. 63/065,699, filed on Aug. 14, 2020.

(51) Int. Cl.
*A61M 1/00* (2006.01)
*A61F 9/007* (2006.01)

(52) U.S. Cl.
CPC ......... *A61M 1/774* (2021.05); *A61F 9/00745* (2013.01); *A61M 2205/3331* (2013.01); *A61M 2210/0612* (2013.01)

(58) Field of Classification Search
CPC .......... A61M 1/774; A61M 2205/3331; A61M 2210/0612; A61M 1/72; A61M 1/743; A61M 2205/128; A61M 2205/3334; A61M 1/77; A61M 1/74; A61M 3/0201; A61M 3/0202; A61M 3/0216; A61M 3/022; A61M 2205/3344; A61M 1/742; A61M 1/7411; A61M 1/804; A61M 2202/09; A61F 9/00745; A61F 9/00736; A61F 9/007; A61F 2009/00887; A61F 2/16; A61F 2009/0087
See application file for complete search history.

(56) References Cited

U.S. PATENT DOCUMENTS

| 4,935,005 A * | 6/1990 | Haines ................. A61M 1/742 604/35 |
| 6,908,451 B2 * | 6/2005 | Brody .................... A61M 1/77 604/27 |
| 8,721,594 B2 | 5/2014 | Zacharias |

(Continued)

*Primary Examiner* — Nicholas J. Weiss
*Assistant Examiner* — Brandon W. Levy

(57) ABSTRACT

According to certain embodiments, a surgical cassette for an ophthalmic surgical system comprises an irrigation conduit that is in fluid communication with a handpiece and carries fluid toward a surgical site. An aspiration conduit is in fluid communication with the handpiece and carries fluid away from the surgical site. An aspiration pump creates a vacuum pressure in the aspiration conduit to draw fluid through the aspiration conduit towards a drain reservoir. A reservoir couples with a pressure-vacuum source to manage the reservoir pressure. A valve is in fluid communication with the aspiration conduit and the reservoir, and provides one or more channels between the aspiration conduit and the reservoir. Each sensor detects a pressure associated with the surgical site. A computer controls the valve in response to the pressure detected by the one or more pressure sensors to mitigate a pressure or volume change.

19 Claims, 9 Drawing Sheets

(56) References Cited

U.S. PATENT DOCUMENTS

| | | |
|---|---|---|
| 2008/0033349 A1* | 2/2008 | Suzuki .................... A61M 1/77 |
| | | 604/35 |
| 2008/0114290 A1* | 5/2008 | King ................... A61M 3/0201 |
| | | 604/30 |
| 2011/0092891 A1* | 4/2011 | Gerg ..................... A61M 39/22 |
| | | 604/28 |
| 2011/0137233 A1 | 6/2011 | Urich et al. |
| 2013/0150782 A1 | 6/2013 | Sorensen |
| 2014/0323953 A1 | 10/2014 | Sorensen et al. |
| 2016/0220751 A1 | 8/2016 | Mallough et al. |
| 2017/0224888 A1* | 8/2017 | Hickey ............... A61M 3/0279 |

* cited by examiner

SYSTEM AND METHOD FOR POST-OCCLUSION SURGE MITIGATION

TECHNICAL FIELD

The present disclosure relates to ophthalmic surgical systems and methods, and more particularly to systems and methods that mitigate post-occlusion surges during ophthalmic surgery.

BACKGROUND

Cataract surgery involves removing the cataractous lens and replacing the lens with an artificial intraocular lens (IOL). The cataractous lens is typically removed by fragmenting the lens and aspirating the lens fragments out of the eye. The lens may be fragmented using, e.g., a phacoemulsification handpiece, a laser handpiece, or other suitable handpiece. During the procedure, the handpiece fragments the lens (using, e.g., ultrasound vibrations or laser energy), and the fragments are aspirated out of the eye through, e.g., a needle. Throughout the procedure, irrigating fluid is pumped into the eye to maintain an intraocular pressure (IOP) to prevent collapse of the eye.

A common complication during the fragmentation process arises from a blockage, or occlusion, of the needle. As the irrigation fluid and emulsified tissue are aspirated through the hollow cutting needle, pieces of tissue that are larger than the needle's bore may clog the tip. When the tip is clogged, vacuum pressure builds up within the tip. An occlusion break occurs when the clog is removed, e.g., the tissue breaks free and moves through the needle. When the clog is removed, the vacuum pressure in the anterior chamber suddenly drops, resulting in a post-occlusion surge. In some cases, the post-occlusion surge can cause a relatively large quantity of fluid and tissue to be aspirated out of the eye too quickly, potentially collapsing the eye and/or tearing the lens capsule.

Various techniques have been designed to mitigate this surge. However, there remains a need for improved ophthalmic systems that mitigate post-occlusion surges as well as maintain a stable IOP throughout varying flow conditions. The present disclosure addresses one or more deficiencies of the prior art.

BRIEF SUMMARY

In certain embodiments, a surgical cassette for an ophthalmic surgical system comprises: an irrigation conduit, an aspiration conduit, an aspiration pump, a reservoir, a valve, one or more pressure sensors, and a computer. The irrigation conduit is in fluid communication with a handpiece and carries fluid toward a surgical site. The aspiration conduit is in fluid communication with the handpiece and carries fluid away from the surgical site. The aspiration pump creates a vacuum pressure in the aspiration conduit to draw fluid through the aspiration conduit towards a drain reservoir. The reservoir holds fluid and couples with a pressure-vacuum source to manage the reservoir pressure of the reservoir. The valve is in fluid communication with the aspiration conduit and the reservoir, and provides one or more channels between the aspiration conduit and the reservoir. Each sensor detects a pressure associated with the surgical site. The computer controls the valve in response to the pressure detected by the one or more pressure sensors to mitigate a pressure and/or volume change.

Embodiments may include none, one, some, or all of the following features:

In certain embodiments, the computer controls the valve to decrease the vacuum pressure in the aspiration conduit when the pressure associated with the surgical site is less than a first pressure threshold.

In certain embodiments, the computer controls the valve to decrease the vacuum pressure by controlling the valve to provide the one or more channels to allow fluid from the reservoir to the aspiration conduit. In certain cases, the computer controls the valve to provide the one or more channels by providing a first channel from the reservoir to the aspiration pump or a second channel from the reservoir to an aspiration connector, the aspiration connector configured to couple to the handpiece. In other cases, the computer controls the valve to provide the one or more channels by providing a first channel from the reservoir to the aspiration pump and a second channel from the reservoir to an aspiration connector, the aspiration connector configured to couple to the handpiece.

In certain embodiments, the first pressure threshold may have a value in the range of 0 to 207 mmHg.

In certain embodiments, a first pressure sensor detects when the pressure associated with the surgical site is less than the first pressure threshold. In certain cases, the first pressure sensor comprises an irrigation pressure sensor configured to detect an irrigation pressure within the irrigation conduit. In other cases, the first pressure sensor comprises an irrigation pressure sensor configured to detect an irrigation pressure at the surgical site. In yet other cases, the first pressure sensor comprises a handpiece pressure sensor located at the handpiece.

In certain embodiments, the computer controls the valve to decrease the vacuum pressure in the aspiration conduit when the pressure associated with the surgical site is less than a first pressure threshold. In certain cases, the computer controls the valve to cease the decrease of the vacuum pressure in the aspiration conduit by controlling the valve to cease allowing the fluid after a predetermined period of time. In other cases, the computer controls the valve to cease the decrease of the vacuum pressure in the aspiration conduit by controlling the valve to cease allowing the fluid when a diverter of the valve reaches a closing angle.

The computer controls the valve to cease the decrease of the vacuum pressure in the aspiration conduit when the pressure associated with the surgical site reaches a second pressure threshold by controlling the valve to cease allowing the fluid. In certain cases, the second pressure threshold has a value in the range of 0 to 760 mmHg. In certain cases, a second pressure sensor detects when the pressure associated with the surgical site reaches the second pressure threshold. The second pressure sensor may comprise an aspiration pressure sensor that detects an aspiration pressure within the aspiration conduit.

In certain embodiments, the surgical cassette further comprises an irrigation pump in fluid communication with the irrigation conduit and the reservoir. The irrigation pump provides irrigation fluid pressure to the reservoir.

In certain embodiments, the pressure-vacuum source maintains the reservoir pressure of the reservoir at a specific pressure with a value in the range of 0 to 500 mmHg.

In certain embodiments, the valve is located at the reservoir.

In certain embodiments, the valve is located along the aspiration conduit and between an aspiration connector and the reservoir. The aspiration connector can be coupled to the handpiece.

In certain embodiments, a surgical cassette for an ophthalmic surgical system comprises: an irrigation conduit, an aspiration conduit, an aspiration pump, a reservoir, a valve, one or more pressure sensors, and a computer. The irrigation conduit is in fluid communication with a handpiece and carries fluid toward a surgical site. The aspiration conduit is in fluid communication with the handpiece and carries fluid away from the surgical site. The aspiration pump creates a vacuum pressure in the aspiration conduit to draw fluid through the aspiration conduit towards a drain reservoir. The reservoir holds fluid and couples with a pressure-vacuum source to manage the reservoir pressure of the reservoir. The valve is in fluid communication with the aspiration conduit, and the reservoir, and the aspiration pump, and provides one or more channels between the aspiration conduit, and the reservoir, and the aspiration pump. Each sensor detects a pressure associated with the surgical site. The computer controls the valve in response to the pressure detected by the one or more pressure sensors to mitigate a pressure and/or volume change.

In certain embodiments, a method for surge mitigation in an ophthalmic surgical system includes: carrying, by an irrigation conduit, fluid toward a surgical site, the irrigation conduit in fluid communication with a handpiece; carrying, by an aspiration conduit, fluid away from the surgical site, the aspiration conduit in fluid communication with the handpiece; creating, by an aspiration pump, a vacuum pressure in the aspiration conduit to draw fluid through the aspiration conduit towards a drain reservoir; providing, by a valve, one or more channels between the aspiration conduit and a reservoir, the reservoir configured to be coupled with a pressure-vacuum source to manage a reservoir pressure of the reservoir, the valve in fluid communication with the aspiration conduit and the reservoir; detecting, by one or more pressure sensors, a pressure associated with the surgical site; and controlling, by a computer, the valve in response to the pressure detected by the one or more pressure sensors to mitigate a pressure and/or volume change.

DESCRIPTION OF EXAMPLE EMBODIMENTS

Figure 1:
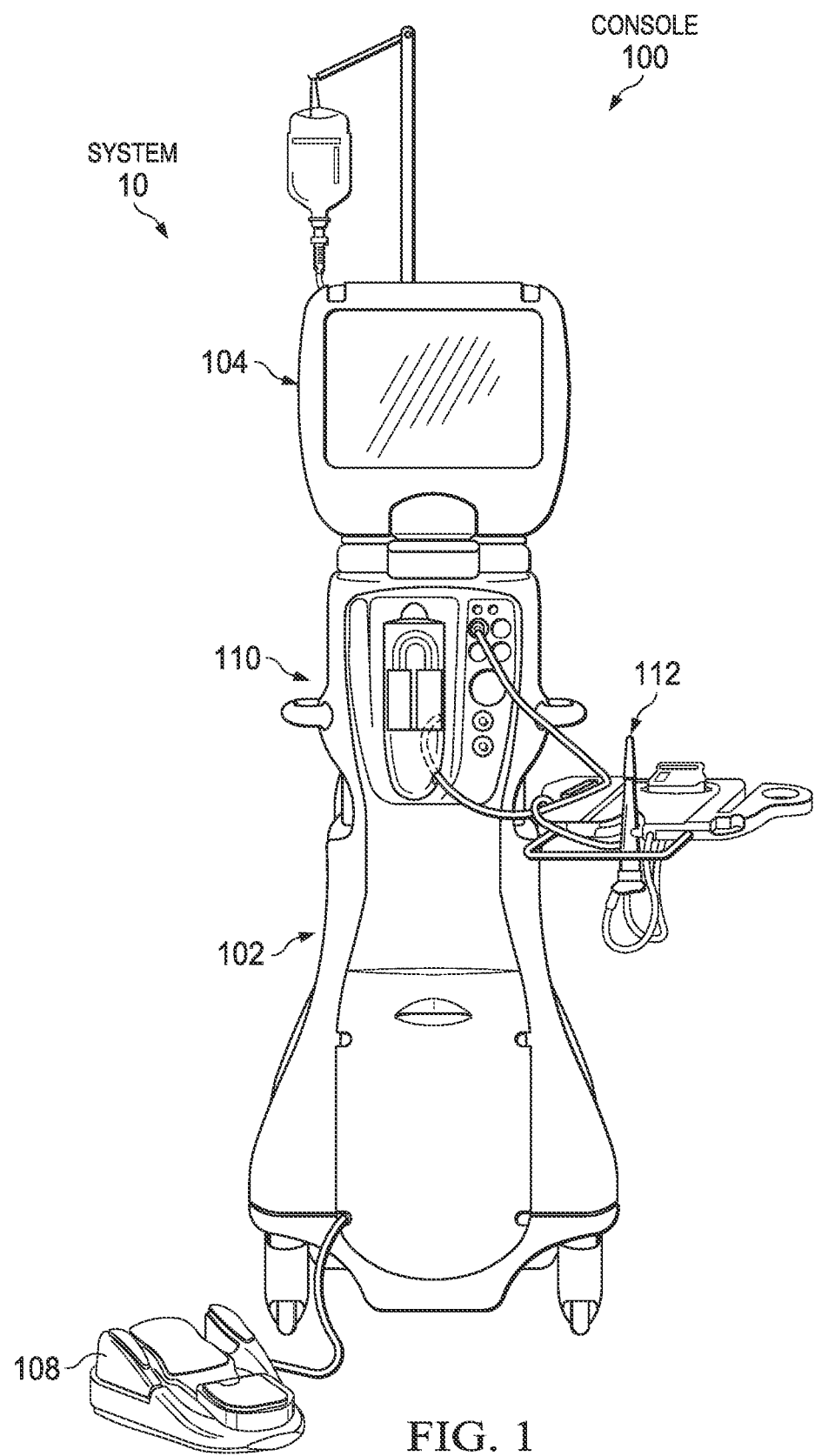
FIG. 1 illustrates an example of an ophthalmic surgical system that may be used to perform ophthalmic procedures on an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for performing lens fragmentation procedures. During fragmentation, mitigating a post-occlusion surge can be critical to the success of the procedure. The devices, system, and methods disclosed herein include a valve and reservoir for mitigating post-occlusion surges. When an occlusion break is detected, a valve allows flow from the reservoir to increase the fluid volume to decrease the vacuum pressure within the aspiration path connected to a handpiece and pump, thereby reducing or preventing a post-occlusion surge. In such a manner, the valve can mitigate a pressure and/or volume change, which may be expressed as a pressure or volume change, with an inclusive "or". The reservoir may be pressurized to allow for more responsive mitigation. Moreover, the valve may allow flow from the reservoir through one or more channels. When pressure has sufficiently recovered, the valve may cease decreasing the vacuum pressure.

FIG. 1 illustrates an example of an ophthalmic surgical system 10 that may be used to perform ophthalmic procedures on an eye. In the illustrated example, system 10 includes the console 100, a housing 102, a display screen 104, a foot pedal 108, a fluidics subsystem 110, and a handpiece 112, coupled as shown and described in more detail with reference to FIG. 2.

Figure 2:
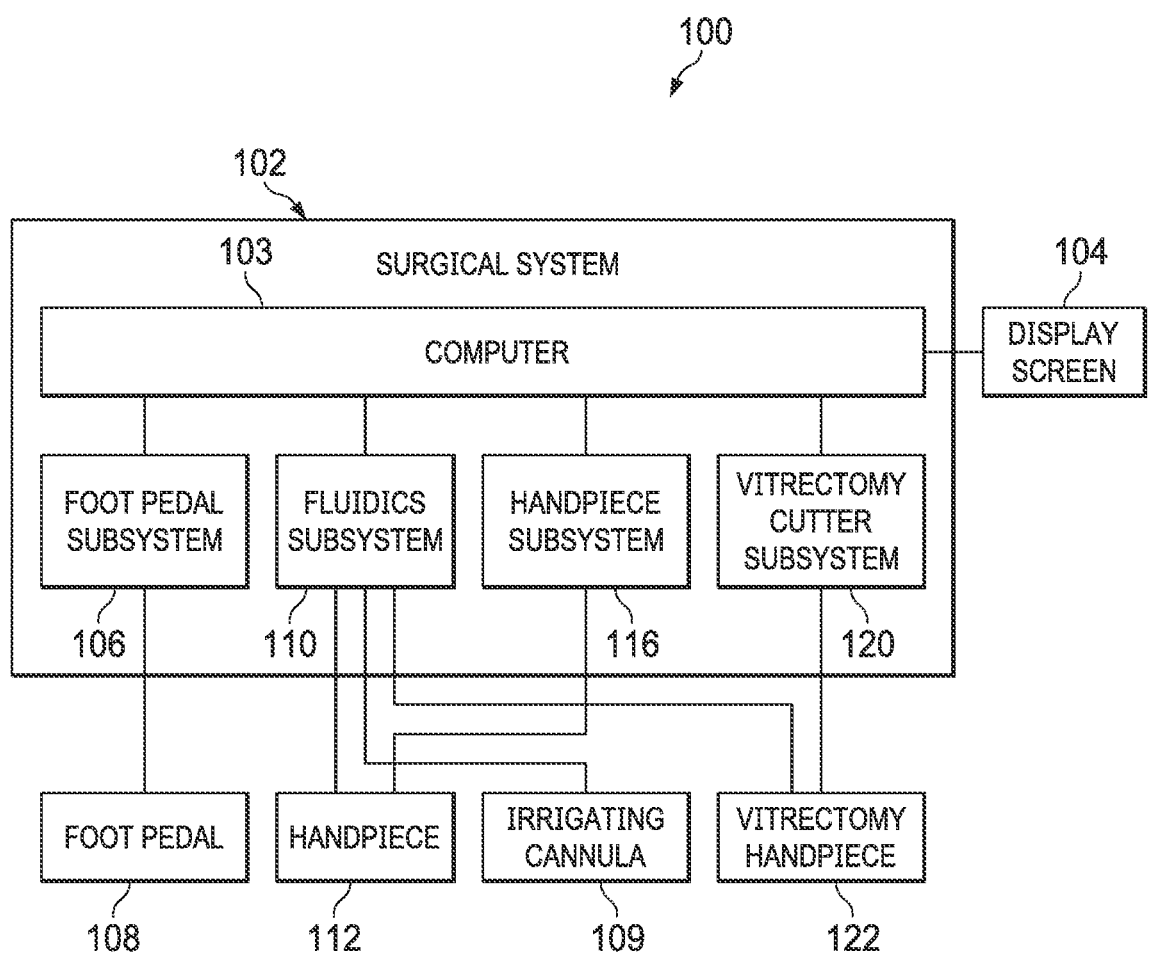
FIG. 2 is a block diagram of a surgical console of the ophthalmic surgical system of FIG. 1.

FIG. 2 is a block diagram of the subsystems of the console 100 of FIG. 1. The console 100 includes a housing 102, which accommodates a computer 103 and subsystems 106, 110, 116, and 120 that support components 108, 112, 109, and 122. A foot pedal subsystem 106 receives input from a foot pedal 108. A fluidics subsystem 110 provides fluid control for a handpiece 112, an irrigating cannula 109, and a vitrectomy handpiece 122. A handpiece subsystem 116 supports the handpiece 112. For example, the subsystem 116 may manage ultrasonic oscillation for a phacoemulsification (phaco) handpiece or may provide laser energy to a laser handpiece. A pneumatic vitrectomy cutter subsystem 120 controls a vitrectomy handpiece 122. A display screen 104 shows data provided by the computer 103.

Figure 3:
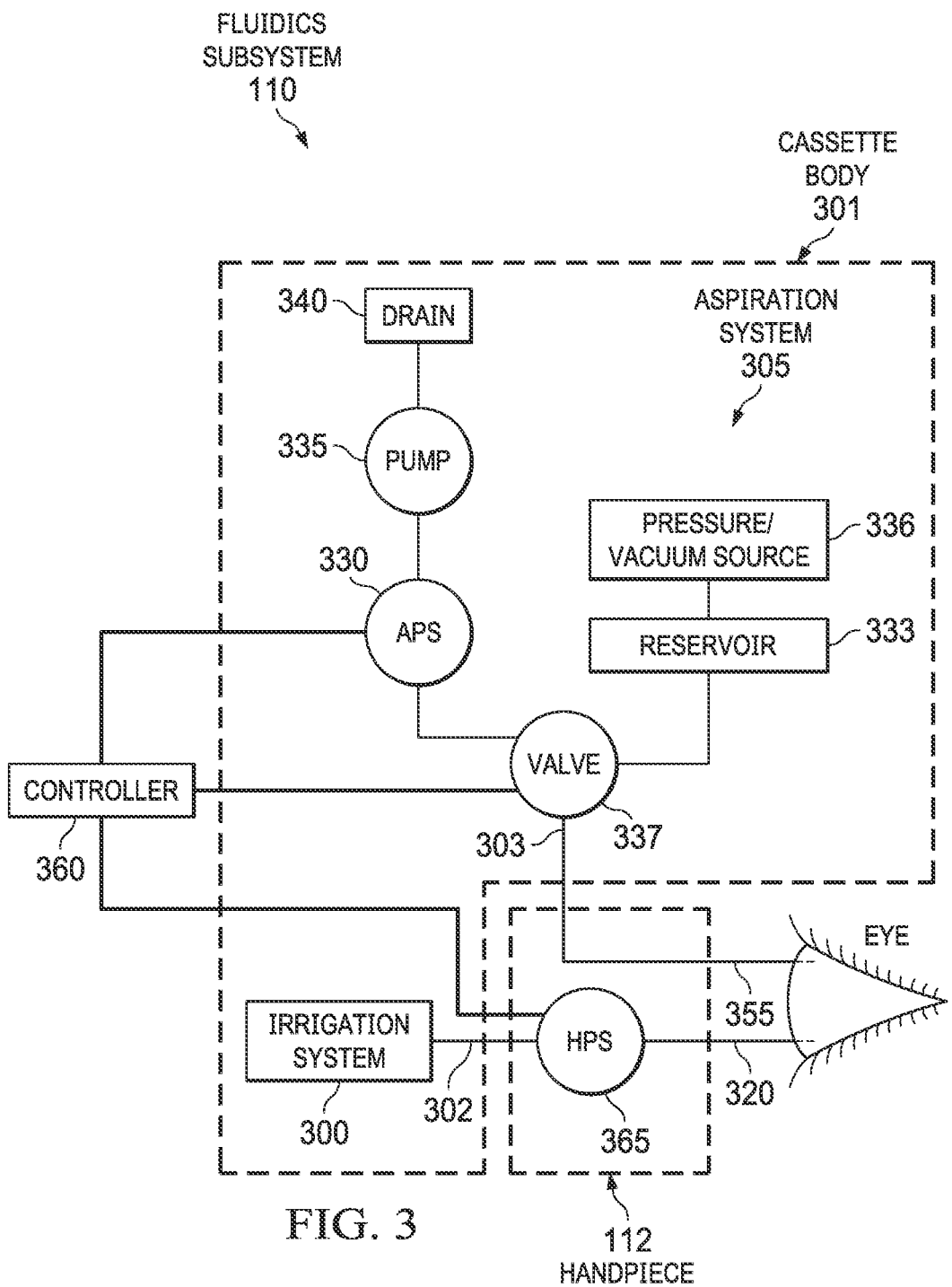
FIG. 3 is a schematic illustrating a fluidics subsystem that may be used with the surgical console of FIGS. 1 and 2.

FIG. 3 is a schematic illustrating the fluidics subsystem 110 that may be used with the surgical console 100 of FIGS. 1 and 2. In general, the computer 103 controls parts of the fluidics subsystem 110 to maintain a target intraocular pressure (IOP) of the eye (which may have a value in the range of 0 to 110 millimeters of mercury (mmHg)) during a surgical procedure. The computer 103 may determine the IOP from measurement of a pressure associated with a surgical site of the eye, or the "surgical site pressure". The surgical site pressure is a pressure (not necessarily measured at the surgical site) that indicates the intraocular pressure (IOP) of the eye. For example, the fluidics subsystem 110 may include a sensor at or inside of the eye that can directly measure the IOP of the eye. The fluidics subsystem 110 may then receive a measurement of the surgical site pressure from the sensor. As another example, the irrigation pressure measured at an irrigation conduit and/or the aspiration pressure measured at an aspiration conduit may indicate the IOP. The surgical site pressure may not be the same as the IOP, but may correspond to the IOP in that a higher surgical site pressure indicates a higher IOP and a lower surgical site pressure indicates a lower IOP. The fluidics subsystem 110 has a variety of sensors 330, 365 (described below) that can measure the surgical site pressure.

The surgical site pressure may have a target range that corresponds to the target IOP of the eye. For example, the irrigation pressure may have a target range of 0 to 110 mmHg (e.g., a value in the range of 0 to 30, 30 to 70, or 70 to 110 mmHg), or the aspiration pressure may have a target range of −760 to 110 mmHg (e.g., a value in the range of −760 to −300, −300 to −100, or −100 to 110 mmHg). If the computer 103 determines the surgical site pressure is outside of the target range, indicating that the IOP is also outside of the target range, the computer 103 controls the fluidics subsystem 110 to bring the pressure back to the target range. For example, to mitigate a post-occlusion surge, a first pressure threshold may indicate when the surgical site pressure is, e.g., below a first threshold in response to an occlusion breakage, and a second pressure threshold may indicate when the surgical site pressure is acceptable, indicating the surgical site pressure has recovered. In certain embodiments, the computer 103 controls a valve to decrease the vacuum pressure in an aspiration conduit when the surgical site pressure is less than the first pressure threshold, and controls the valve to cease decreasing the vacuum pressure when the surgical site pressure the reaches a second pressure threshold, after a certain period of time has passed, or after a diverter of a valve reaches a closing angle.

In the illustrated example, the fluidics subsystem 110 has a cassette body 301 that may be accommodated by the surgical console 100 as a surgical cassette. The fluidics subsystem 110 includes an irrigation system 300 and an aspiration system 305, which are controlled by a computer 103 such as a controller 360. The irrigation system 300 and aspiration system 305 are in fluid communication with the handpiece 112. Parts that are in fluid communication with each other are parts for which fluid is allowed to flow between (to and/or from) the parts.

Console 100 may include one or more handpieces 112, including an ultrasonically-driven phaco handpiece, a laser handpiece, and/or other suitable handpiece. In certain embodiments, the handpiece 112 may be an ultrasonically-driven phaco handpiece. In the illustrated example, the phaco handpiece 112 includes an irrigating part 320, a cutting needle 355, and a handpiece pressure sensor (HPS) 365. The irrigating part 320 provides fluid to the surgical site, and may be an irrigating tip or an irrigating sleeve that surrounds the needle 355. The cutting needle 355 is a hollow needle that vibrates at a fixed frequency to break up tissue. Fluid and tissue may be aspirated through the needle 355.

In certain embodiments, the handpiece 112 may be a laser handpiece. A laser handpiece uses laser energy to fragment the lens to facilitate the phacoemulsification process. In the embodiments, the fluidics subsystem 110 supports the laser handpiece (e.g., provides irrigation and aspiration functions) in a manner similar to that of a phaco handpiece. In certain embodiments, the laser handpiece may include a sensor that measures the surgical site pressure to provide a measurement for post-occlusion mitigation.

The HPS 365 is an irrigation pressure sensor that detects the irrigation pressure within the irrigation conduit 302. In the illustrated example, the HPS 365 is located on the handpiece 112 close to the surgical site, e.g., less than 12 inches from the surgical site. The proximity to the surgical site may enable quick detection of changes in pressure (as may occur during an occlusion break) and allow for real-time surge suppression. In some examples, HPS 365 detects pressure changes within 50 milliseconds of an occlusion break, which may enable the controller 360 to respond to pressure deviations before IOP is overly negatively affected. In general, an irrigation pressure sensor may be located at any suitable location, such as any suitable location of the handpiece 112 (e.g., the proximal end, the distal end, or proximate the irrigating part 320), at any suitable location along an irrigation conduit, or at any suitable component in fluid communication with the surgical site (e.g., within in a separate tube or probe).

The aspiration system 305 carries fluid away from the surgical site towards a drain reservoir 340 by creating and maintaining a vacuum pressure (or negative pressure) in aspiration conduits 303. Vacuum pressure can be described as negative pressure. Accordingly, increasing the vacuum pressure may be described as increasing negative pressure or decreasing pressure, and decreasing the vacuum pressure may be described as decreasing negative pressure or increasing pressure.

The aspiration system 305 includes an aspiration conduit 303, a valve 337, a reservoir 333, a pressure-vacuum source 336, an aspiration pressure sensor (APS) 330, an aspiration pump 335, and a drain reservoir 340 in fluid communication along aspiration paths as shown. The aspiration conduit 303 provides fluid communication between the aspiration system 305 and the handpiece 112. In the illustrated example, the aspiration conduit 303 aspirates from the needle 355 of the handpiece 112. The reservoir 333 stores fluid that may be used for surge mitigation. Pressure-vacuum source 336 maintains and adjusts the reservoir pressure of reservoir 333. For surge mitigation, the reservoir pressure may be in the range of 0 to 500 mmHg (e.g., a value in the range of 0 to 100, 100 to 400, or 400 to 500 mmHg). Examples of the reservoir 333 include a venturi, drain, vent, irrigation, and other suitable reservoir, and the reservoir 333 may be implemented as one or more reservoirs.

The valve 337 controls flow to and/or from the reservoir 333 for the handpiece 112. Valve 337 controls the vacuum pressure within the aspiration conduit 303 by opening and/or closing channels in order to mitigate the effects of a post-occlusion surge. Examples of the valve 337 include a vent, drain, rotary, variable vacuum relief, and other suitable valve, and the valve 337 may be implemented as one or more valves. The valve 337 may be located at any suitable location of the fluidics subsystem 110. For example, the valve 337 may be located closer to the eye, e.g., proximate to an aspiration connector, which may improve mitigation performance. As another example, the valve 337 may be located at the reservoir 333 or along the aspiration conduit 303 between an aspiration connector and the reservoir 333. Valve operations are described in more detail with reference to FIGS. 4A to 4F.

APS 330 detects the aspiration pressure within aspiration conduit 303. The aspiration pump 335 creates a vacuum pressure within the aspiration conduit 303 between the pump 335 and the eye to draw fluid from the surgical site and into the drain reservoir 340. The pump 335 may be, e.g., a dual segment elastomer pump. The drain reservoir 340 receives the fluid from the surgical site. Drain reservoir 340 may be a bag or an intersection of conduits that receives fluid within the cassette body 301.

The controller 360 is a computer that controls parts of the fluidics subsystem 110, such as valves (e.g., 337) and pumps (e.g., 335), in response to pressure sensors (e.g., 330, 365, a sensor at or inside of the eye) to control pressure within conduits 302, 303 in order to maintain a target pressure at the surgical site. In certain embodiments, the controller 360 controls the valve 337 to mitigate a post-occlusion surge. In the embodiments, the computer 103 controls the valve 337 to decrease the vacuum pressure in an aspiration conduit when the surgical site pressure is less than the first pressure threshold, and controls the valve to cease decreasing the vacuum pressure when the surgical site pressure the reaches a second pressure threshold, after a certain period of time has passed, or after a diverter of a valve reaches a closing angle.

The controller 360 may open and/or close channels of the valve 337 to adjust the vacuum pressure in the aspiration conduit 303. A channel is opened by making the passageway of the channel larger. A channel that is opened to allow for maximum fluid flow is fully opened; otherwise, the channel is partially opened. A channel is closed by making the passageway of the channel smaller. A channel that is closed such that no fluid passed through is fully closed; otherwise, channel is partially closed.

In some embodiments, the controller 360 regulates the amount that a channel is opened or closed (i.e., the size of the passageway of the channel) based on the deviation between the detected pressure and a target pressure. For example, for a larger deviation, the passageway may be larger to allow more fluid. For a smaller deviation, the passageway may be smaller to allow less fluid. In these examples, as a detected pressure reaches a target pressure, the deviation decreases, so the passageway may be made smaller.

In certain embodiments, the controller 360 may have access to a memory that stores one or more pressure thresholds, and may perform an action in response to a detected pressure reaching a pressure threshold. For example, when a detected pressure reaches a pressure threshold, the controller 360 controls a valve to adjust the pressure. In certain embodiments, a first pressure threshold may indicate that the pressure associated with the surgical site has rapidly decreased to an unacceptable level, such as in response to an occlusion break. In response, the controller 360 decreases the vacuum pressure in the aspiration conduit 303 to mitigate the rapid decrease of the surgical site pressure. A second pressure threshold may indicate that the surgical site pressure has recovered. In response, the controller 360 ceases decreasing the vacuum pressure in the aspiration conduit 303.

The controller may determine the surgical site pressure from one or more suitable sensors. In certain embodiments, a decrease in irrigation pressure may indicate a drop in the surgical site pressure in response to, e.g., an occlusion break. In the illustrated example, one or more irrigation pressure sensors (e.g., HPS 365) detect the irrigation pressure within the irrigation conduit 302. The first pressure threshold may define the irrigation pressure at which the controller 360 should decrease the vacuum pressure, and may have any suitable value, e.g., a value in the range of 0 to 207 mmHg (e.g., a value in the range of 0 to 35, 35 to 100, or 100 to 207 mmHg).

In certain embodiments, an aspiration pressure may indicate when an acceptable surgical site pressure has been reached in response to mitigating the post-occlusion surge. In the illustrated example, the aspiration pressure sensor 330 detects the aspiration pressure. The second pressure threshold may define the aspiration pressure at which the controller 360 should stop decreasing the vacuum pressure, and may have any suitable value, e.g., a value in the range of 0 to 760 mmHg (e.g., a value in the range of 0 to 30, 30 to 300, or 300 to 760 mmHg). In some embodiments, the second pressure threshold may be selected such that the controller 360 stops decreasing the vacuum pressure before the target IOP range is reached, since the vacuum pressure typically continues to decrease for a short while after the controller 360 acts to stop the decrease.

While the above example uses a first pressure threshold defined in terms of an irrigation pressure and a second pressure threshold defined in terms of an aspiration pressure, the first and second thresholds may be defined in terms of use suitable type of pressure (e.g., aspiration pressure, an irrigation pressure, or an intraocular pressure) from any suitable sensors that indicate the pressure at the surgical site. In addition, the first and/or second thresholds can be defined in terms of the same or different types of pressure, e.g., both thresholds could be defined in terms of an aspiration pressure.

FIGS. 4A through 4F illustrate examples of operations a valve, such as the valve 337, may be controlled to perform. In certain embodiments, a controller may move a diverter to an opening angle to open a channel of a rotary valve. As fluid flows through the channel and pressure is reduced, the diverter may move in the opposite direction. When the diverter reaches a closing angle indicating reduction to a desired pressure, the controller may close the channel. The opening and closing angles may be selected based on the operation of the particular valve in a particular fluidics subsystem 110, in particular the pressures achieved when the diverter is at particular angles in a particular fluidics subsystem 110. These angles may be determined by operating the diverter at different angles in the fluidics subsystem 110 and noting the resulting pressures.

Figure 4C:
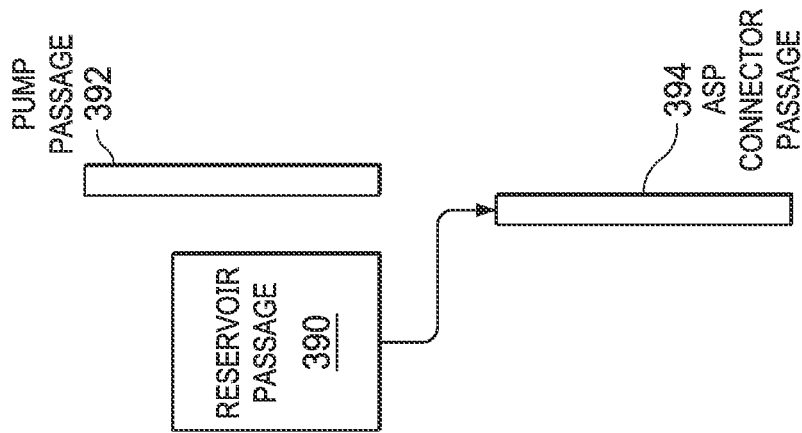
FIGS. 4A through 4F illustrate examples of operations that a valve of the fluidics subsystem of FIG. 3 may perform.
Figure 4B:
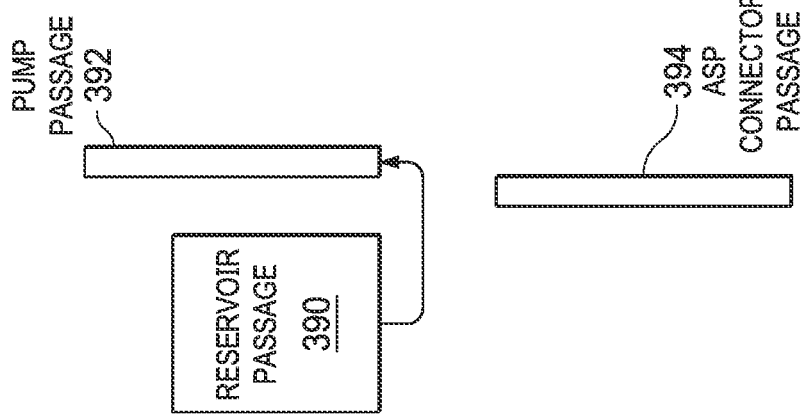
Figure 4A:
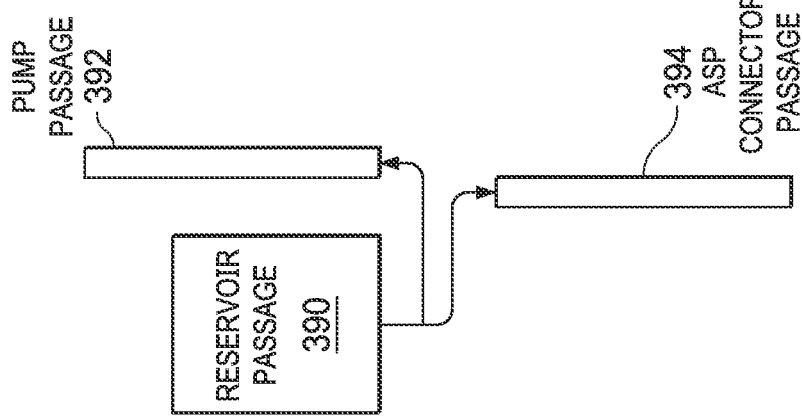

(1) Venting of Reservoir. During venting (e.g., for surge mitigation), a channel from the reservoir 333 to the aspiration pump 335 and/or a channel from the reservoir 333 to an aspiration connector may be opened. FIG. 4A shows a channel from the reservoir 333 via a reservoir passage 390 to the aspiration pump 335 via a pump passage 392, and a channel from the reservoir 333 via the reservoir passage 390 to the aspiration connector via an aspiration connector passage 394, for dual venting. FIG. 4B shows a channel from the reservoir 333 via reservoir passage 390 to the aspiration pump 335 via the pump passage 392, for reservoir draining or for reservoir driven reflux to suction path. FIG. 4C shows a channel from the reservoir 333 via reservoir passage 390 to the aspiration connector via the aspiration connector passage 394, for aspiration or for reservoir driven reflux.

The selection of channels to open may be made according to any suitable factors. For example, if there is a large deviation between the detected pressure and the pressure threshold, both channels may be opened to increase flow and more rapidly vent the stored vacuum. A large deviation may have a value between, e.g., 0 to 35 mmHg (e.g., a value in the range of 0 to 10, 10 to 20, or 20 to 35 mmHg).

Figure 4D:
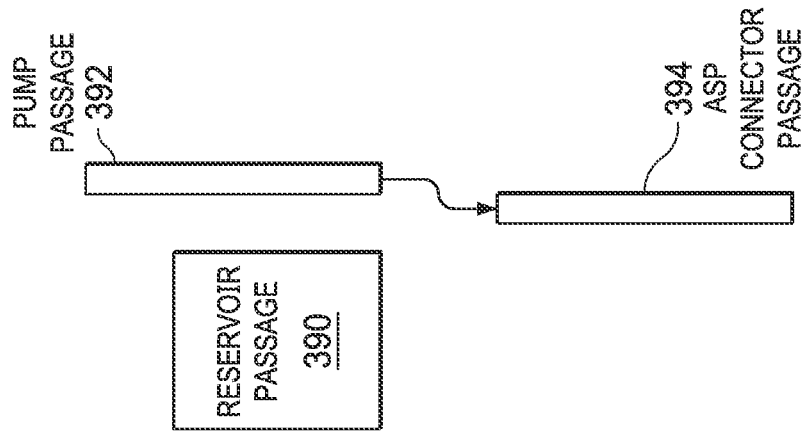

(2) Reservoir Maintenance. In one example of maintaining a fluid level in the reservoir 333, channels from the aspiration connector to the reservoir 333 and from the reservoir 333 to the aspiration pump 335 may be opened, such that the valve 337 supports different flows with different channels. The pressure-vacuum source 336 may enable a vacuum in the reservoir 333 to facilitate the flow from the aspiration connector. FIG. 4D shows a channel from the aspiration connector via the aspiration connector passage 394 to the reservoir 333 via reservoir passage 390, and a channel from the reservoir 333 via reservoir passage 390 to the aspiration pump 335 via the pump passage 392, for reservoir driven aspiration with drain pumping.

Figure 4E:
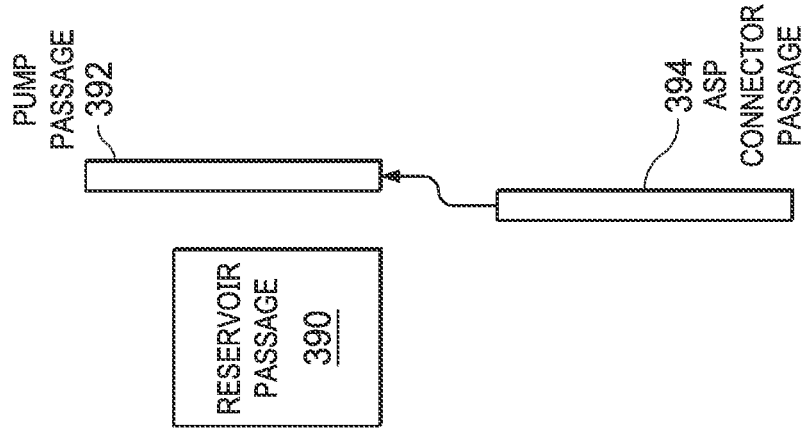
Figure 4F:
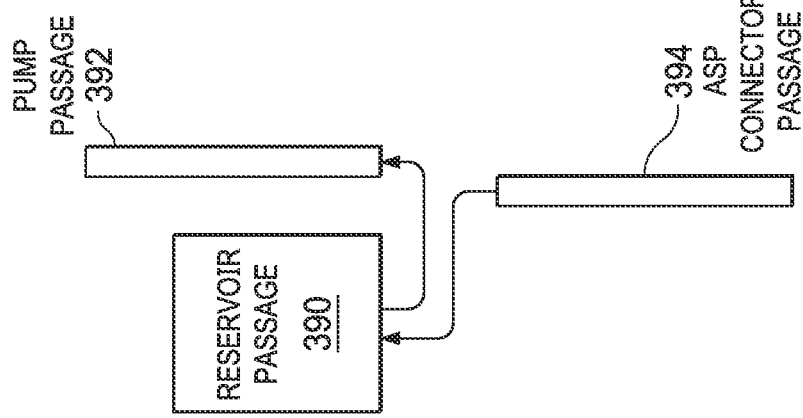
Figure 5C:
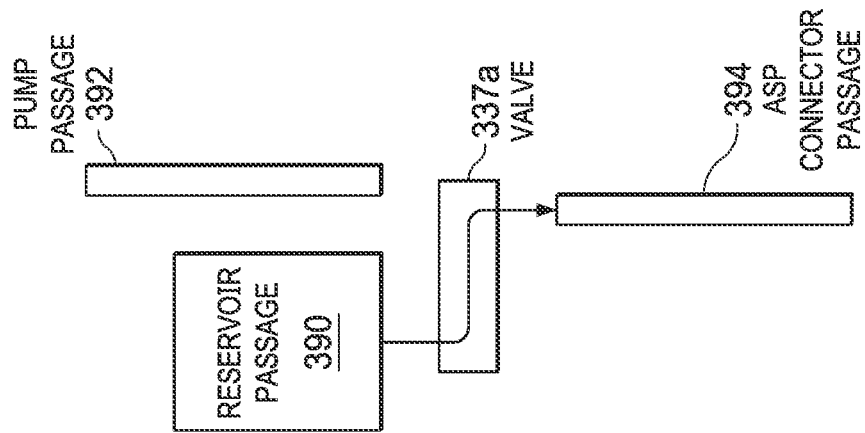
FIGS. 5A through 5F illustrate examples of operations a valve that may be controlled to perform the operations of the valve of FIGS. 4A through 4F, respectively.
Figure 5B:
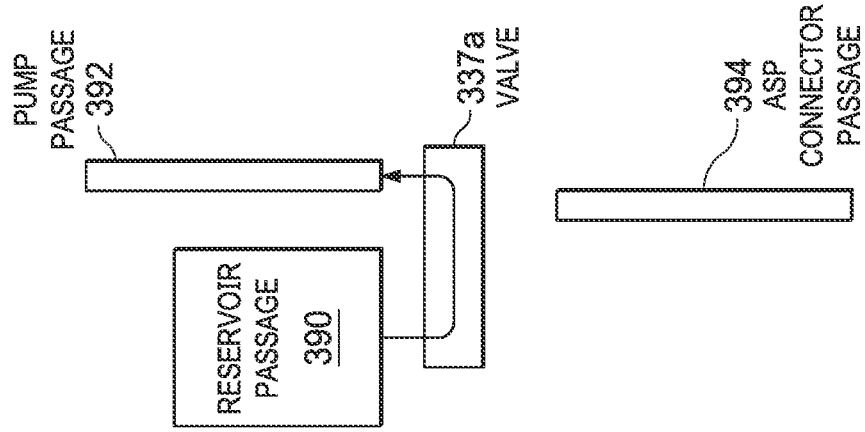
Figure 5A:
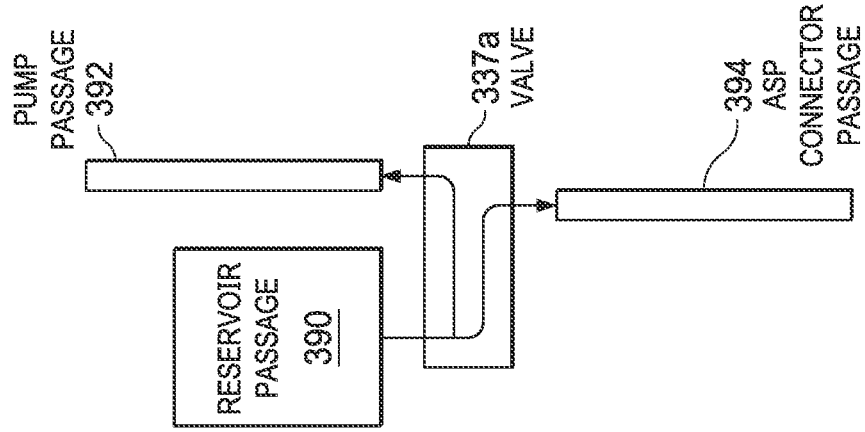
Figure 5D:
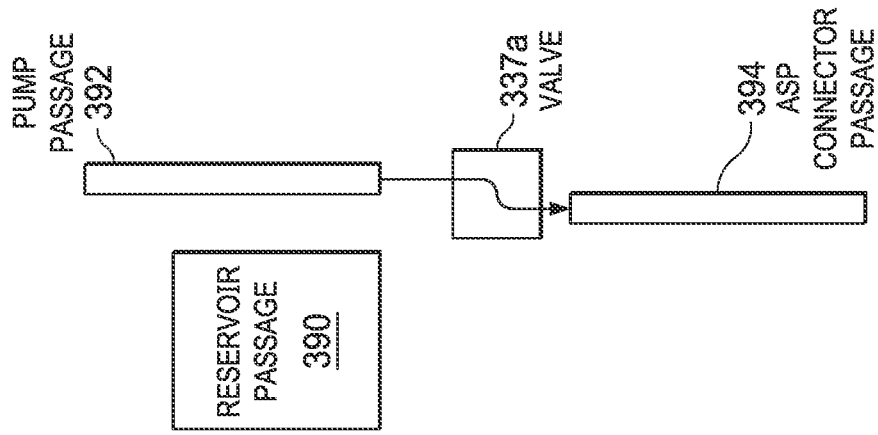
Figure 5E:
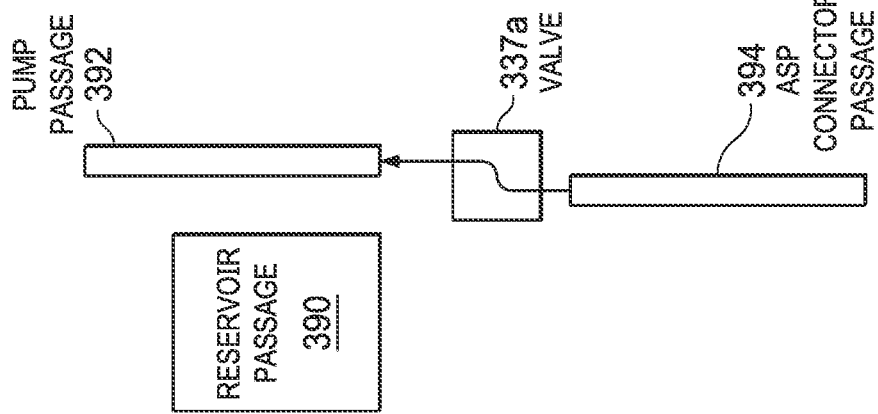
Figure 5F:
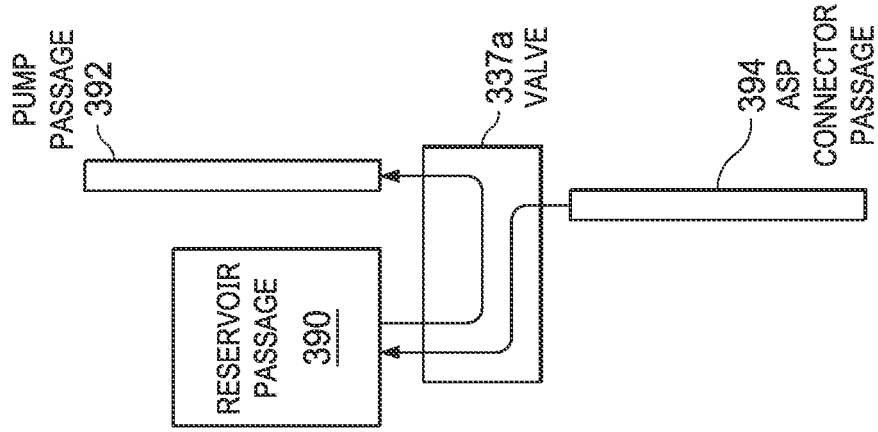

(3) Aspiration Pump-Connector Channels. A channel between an aspiration connector and aspiration pump 335 (e.g., from the aspiration connector to aspiration pump 335 and/or from aspiration pump 335 to the aspiration connector) may be opened. FIG. 4E shows a channel from the aspiration connector via the aspiration connector passage 394 to the aspiration pump 335 via the pump passage 392, for aspiration driven directly by pumping. FIG. 4F shows a channel from the aspiration pump 335 via the pump passage 392 to the aspiration connector via the aspiration connector passage 394, for pump driven reflux. In certain embodiments, to prevent fluid from entering or exiting reservoir 333, any channel to reservoir 333 may be closed and/or the pressure-vacuum source 336 may be disabled.

FIGS. 5A through 5F illustrate examples of operations a valve 337a that may be controlled to perform the operations of the valve of FIGS. 4A through 4F, respectively. The valve 337a may be any suitable valve, e.g., a single channel valve that can provide dual paths.

Figure 6:
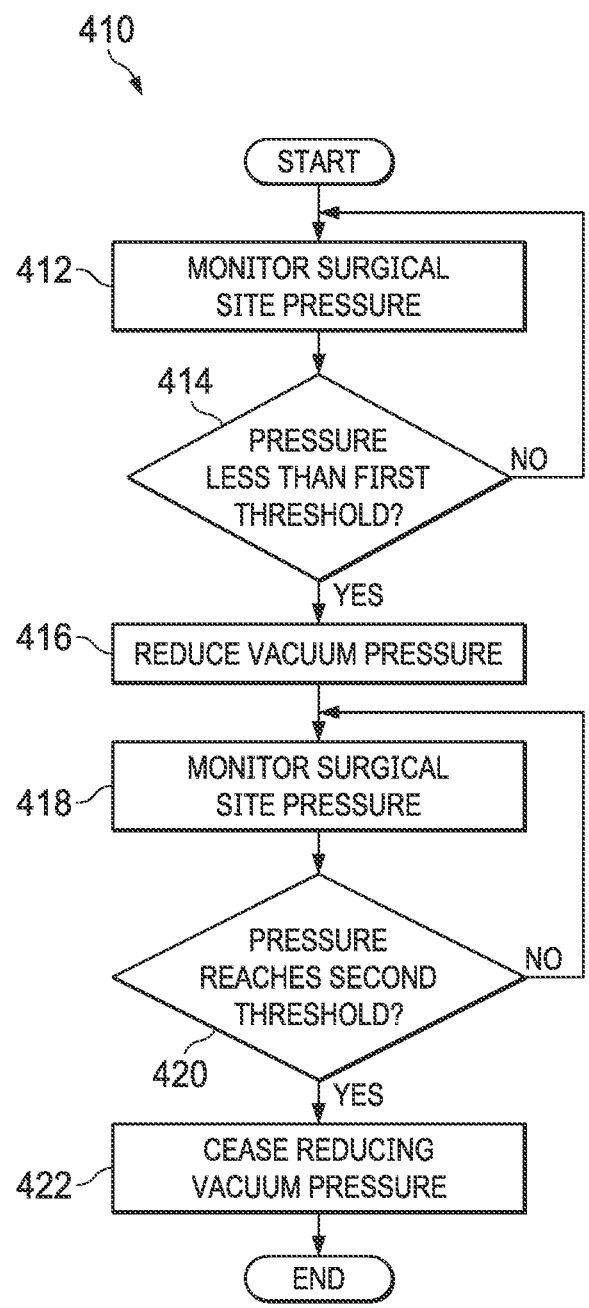
FIG. 6 illustrates an example of a method that may be used by the fluidics subsystem of FIG. 3 to mitigate a post-occlusion surge.

FIG. 6 illustrates an example of a method 410 that may be used by the fluidics subsystem 110 of FIG. 3 to mitigate a post-occlusion surge. The method starts at step 412, where the controller 360 monitors a pressure associated with the surgical site. The controller 360 may use any suitable sensor to measure the surgical site pressure at steps 412 and 418, e.g., a sensor of the fluidics subsystem 110 or a sensor at or inside of the eye that directly measures IOP of the eye. In certain examples, the controller 360 may use an irrigation sensor (e.g., HPS 365) to measure irrigation pressure as the surgical site pressure. The controller 360 determines whether the surgical site pressure has decreased below a first pressure threshold at step 414, indicating that, e.g., an occlusion break has occurred. If there is no such decrease, the method returns to step 412, where the controller 360 continues to monitor the surgical site pressure. If there is such a decrease, the method proceeds to step 416.

The controller 360 reduces the vacuum pressure at step 416 to initiate returning the surgical site pressure to a target range. In certain examples, the controller 360 may reduce the vacuum pressure by opening one or more channels of the valve 337 to allow fluid to flow from the reservoir 333 to the aspiration conduit 303. The controller 360 monitors the surgical site pressure at step 418. In certain examples, the controller 360 may measure the aspiration pressure using an aspiration pressure sensor 330 as the surgical site pressure.

At step 420, the controller 360 determines whether the surgical site pressure has reached (e.g., is equal to or greater than) a second pressure threshold. If the surgical site pressure has not reached the second pressure threshold, then the method returns to step 418 to continue to monitor the surgical site pressure. If the surgical site pressure has reached the second pressure threshold, then the method proceeds to step 422, where the controller ceases reducing the vacuum pressure at step 410. In certain examples, the controller 360 closes the one or more channels to cease reducing the vacuum pressure. The method for mitigating a post-occlusion surge then ends.

Figure 7:
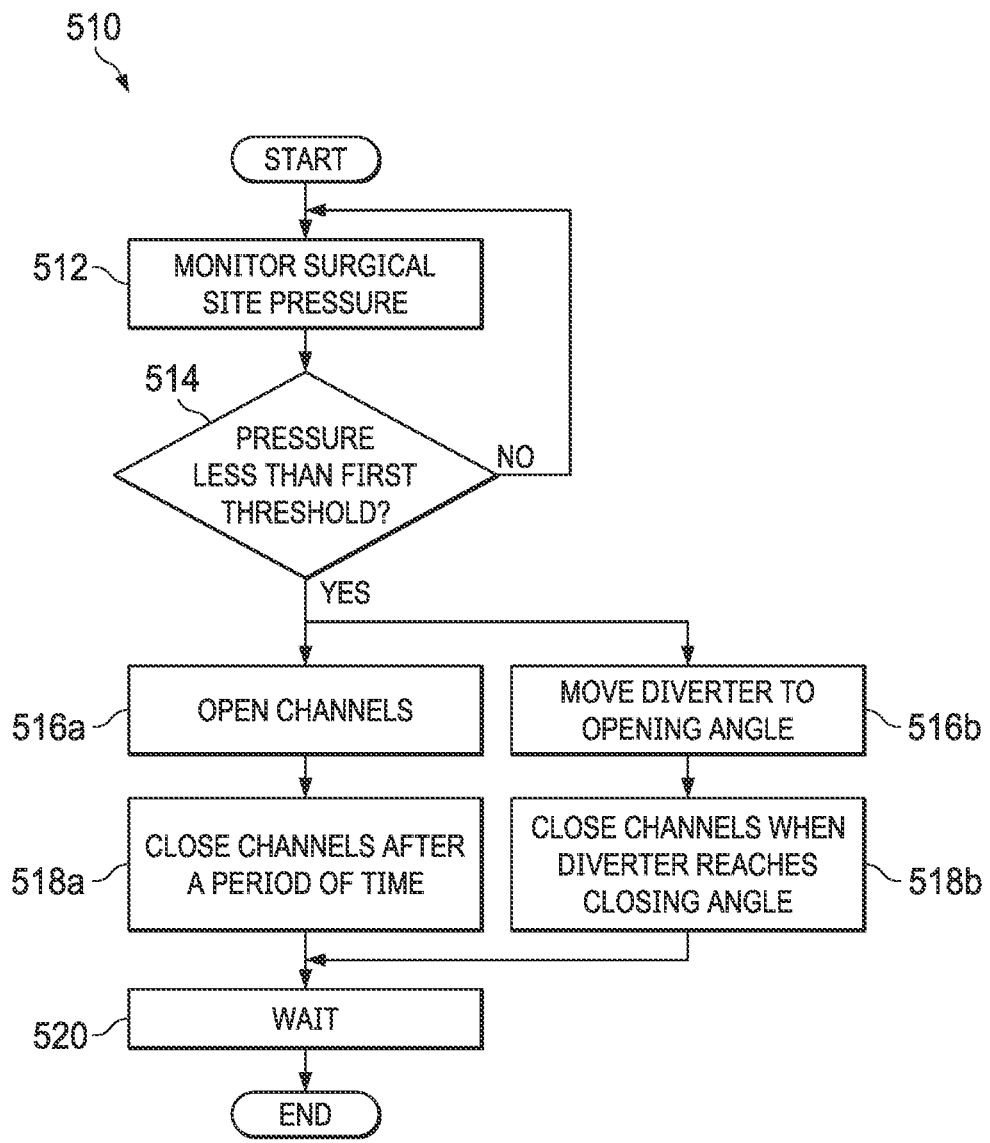
FIG. 7 illustrates another example of a method that may be used by the fluidics subsystem of FIG. 3 to mitigate a post-occlusion surge.

FIG. 7 illustrates another example of a method 510 that may be used by the fluidics subsystem 110 of FIG. 3 to mitigate a post-occlusion surge. Steps 512 and 514 are analogous to steps 412 and 414 of FIG. 5.

In certain embodiments, the fluidics subsystem 110 performs steps 516a and 518a, and in other embodiments, the fluidics subsystem 110 performs steps 516b and 518b. In certain embodiments, at step 516a, the controller 360 opens one or more channels of the valve 337 to allow fluid to flow in order to reduce the vacuum pressure. The controller 360 closes the one or more channels at step 518a after a predetermined period of time. The predetermined period of time may have any suitable value, e.g., a value between 1 millisecond and 10 seconds.

In other embodiments, at step 516b, the controller 360 moves a diverter of the valve 337 in the rotation direction to an opening angle to open one or more channels to allow fluid to flow in order to reduce the vacuum pressure. As the pressure reduces, the diverter moves in the opposite direction. The controller 360 closes the one or more channels at step 518b after the diverter reaches a closing angle. The opening and closing angles may be selected based on the operation of the particular valve 337 in a particular fluidics subsystem 110, specifically, based on the pressures achieved when the diverter is at particular angles in the fluidics subsystem 110.

The controller 360 waits for a waiting period before continuing with normal operation at step 520. The waiting period allows for the fluidics subsystem 110 to normalize after the occlusion break. The waiting period may have any suitable value, e.g., a value less than 10 seconds. The method for mitigating a post-occlusion surge then ends.

A component (such as the computer 103 or controller 360) of the systems and apparatuses disclosed herein may include an interface, logic, and/or memory, any of which may include hardware and/or software. An interface can receive input to the component, send output from the component, and/or process the input and/or output. Logic can perform operations of the component. Logic may include one or more electronic devices that process data, e.g., execute instructions to generate output from input. Examples of such an electronic device include a computer, processor or microprocessor (e.g., a Central Processing Unit (CPU), and computer chip. Logic may include computer software that encodes instructions capable of being executed by the electronic device to perform operations. Examples of computer software includes a computer program, an application, and an operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database and/or network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components. As another example, modifications may be made to the methods disclosed herein. The methods may include more, fewer, or other steps, and the steps may be performed in any suitable order.

To aid the Patent Office and readers in interpreting the claims, Applicants wish to note that they do not intend any of the claims or claim elements to invoke 35 U.S.C. § 112(f) unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. A surgical system, comprising:
   an irrigation conduit in fluid communication with a handpiece and configured to carry fluid toward a surgical site;
   an aspiration conduit in fluid communication with the handpiece and configured to carry fluid away from the surgical site;
   an aspiration pump configured to create a vacuum pressure in the aspiration conduit to draw fluid through the aspiration conduit towards a drain reservoir;
   a venturi reservoir configured to hold fluid at a controlled reservoir pressure;
   a rotary valve located at the venturi reservoir; wherein the rotary valve comprises:
      one or more first channels to provide fluid communication between the venturi reservoir and the aspiration conduit;
      one or more second channels to provide fluid communication between the venturi reservoir and the aspiration pump;
      wherein at least one position of the rotary valve provides dual venting by providing fluid communication between the venturi reservoir and the aspiration conduit and fluid communication between the venturi reservoir and the aspiration pump;
   a first pressure sensor configured to detect a pressure associated with the surgical site; and
   a computer configured to control the rotary valve in response to the pressure detected by the first pressure sensor.

2. The system of claim 1, the computer further configured to:
   control the rotary valve to decrease the vacuum pressure in the aspiration conduit when the pressure associated with the surgical site is less than a first pressure threshold.

3. The system of claim 2, the computer further configured to:
   control the rotary valve to decrease the vacuum pressure by controlling the rotary valve to allow fluid from the venturi reservoir to the aspiration conduit.

4. The system of claim 3,
   wherein controlling the rotary valve to allow fluid from the venturi reservoir to the aspiration conduit comprises providing a channel of the one or more first channels from the venturi reservoir to an aspiration connector, the aspiration connector configured to couple to the handpiece.

5. The system of claim 3, the computer further configured to:
   control the rotary valve to simultaneously provide the one or more first channels between the aspiration conduit and the venturi reservoir and the one or more second channels between the venturi reservoir and the aspiration pump for dual venting.

6. The system of claim 2, the first pressure threshold having a value in the range of 0 to 207 mmHg (millimeters of mercury).

7. The system of claim 2 wherein the first pressure sensor detects when the pressure associated with the surgical site is less than the first pressure threshold.

8. The system of claim 7, the first pressure sensor comprising an irrigation pressure sensor configured to detect an irrigation pressure within the irrigation conduit.

9. The system of claim 7, the first pressure sensor comprising an irrigation pressure sensor configured to detect an irrigation pressure at the surgical site.

10. The system of claim 7, the first pressure sensor located at the handpiece.

11. The system of claim 2, the computer further configured to:
    control the rotary valve to cease the decrease of the vacuum pressure in the aspiration conduit by controlling the rotary valve to cease allowing the fluid after a predetermined period of time.

12. The system of claim 2, the computer further configured to:
    control the rotary valve to cease the decrease of the vacuum pressure in the aspiration conduit by controlling the rotary valve to cease allowing the fluid when a diverter of the rotary valve reaches a closing angle.

13. The system of claim 2, the computer further configured to:
    control the rotary valve to cease the decrease of the vacuum pressure in the aspiration conduit when the pressure associated with the surgical site reaches a second pressure threshold by controlling the rotary valve to cease allowing the fluid.

14. The system of claim 13, the second pressure threshold having a value in the range of 0 to 760 mmHg.

15. The system of claim 13 further comprising a second pressure sensor, the second pressure sensor detects when the pressure associated with the surgical site reaches the second pressure threshold.

16. The system of claim 15, the second pressure sensor comprising an aspiration pressure sensor configured to detect an aspiration pressure within the aspiration conduit.

17. The system of claim 1, wherein the reservoir pressure of the venturi reservoir is maintained at a specific pressure with a value in the range of 0 to 500 mmHg.

18. The system of claim 1, the rotary valve located along the aspiration conduit and between an aspiration connector and the venturi reservoir, the aspiration connector configured to couple to the handpiece.

19. The system of claim 1, wherein the computer is further configured to disable a pressure-vacuum source coupled to the venturi reservoir.

* * * * *